(12) United States Patent
Richard et al.

(10) Patent No.: US 10,571,405 B2
(45) Date of Patent: Feb. 25, 2020

(54) QUALITY CONTROL STATION FOR A SHEET ELEMENT PROCESSING MACHINE AND ILLUMINATION UNIT FOR THE QUALITY CONTROL STATION

(71) Applicant: BOBST MEX SA, Mex (CH)

(72) Inventors: Matthieu Richard, Remoray (FR); Francis Pilloud, Clarens (CH)

(73) Assignee: BOBST MEX SA (CH)

( * ) Notice: Subject to any disclaimer, the term of this patent is extended or adjusted under 35 U.S.C. 154(b) by 0 days.

(21) Appl. No.: 16/099,706

(22) PCT Filed: May 17, 2017

(86) PCT No.: PCT/EP2017/025132
§ 371 (c)(1),
(2) Date: Nov. 8, 2018

(87) PCT Pub. No.: WO2017/207113
PCT Pub. Date: Dec. 7, 2017

(65) Prior Publication Data
US 2019/0154589 A1    May 23, 2019

(30) Foreign Application Priority Data
May 30, 2016    (EP) .................................... 16172030

(51) Int. Cl.
G01N 21/89 (2006.01)
(52) U.S. Cl.
CPC ..... G01N 21/8914 (2013.01); G01N 21/8901 (2013.01); *G01N 2021/8905* (2013.01);
(Continued)

(58) Field of Classification Search
CPC ............... G01N 21/86; G01N 21/8803; G01N 21/8806; G01N 21/89; G01N 21/896; G01N 21/958
(Continued)

(56) References Cited

U.S. PATENT DOCUMENTS 3,702,930 A    11/1972    Joel .......................... 240/41.35 R
6,170,973 B1 *  1/2001    Benedict ............ G01N 21/8901
                                                            348/E5.029
(Continued)

FOREIGN PATENT DOCUMENTS

DE    100 00 029 A1    7/2001

OTHER PUBLICATIONS

International Search Report dated Jul. 11, 2017 in corresponding PCT International Application No. PCT/EP2017/025132.
(Continued)

*Primary Examiner* — Hoa Q Pham
(74) *Attorney, Agent, or Firm* — Ostrolenk Faber LLP

(57) ABSTRACT

A quality control station (2) for a sheet element processing machine, having at least one camera (6) arranged for capturing images of sheet elements (4) transported through the quality control station (2), and further having an illumination unit (5) with at least one light emitter (16) and two reflectors (12, 14), the illumination unit (5) directing light onto a viewing area of the camera (6) such that the illumination intensity is constant despite changing media thickness. An illumination unit for such quality control station is disclosed.

14 Claims, 3 Drawing Sheets

(52) U.S. Cl.
CPC .............. *G01N 2021/8908* (2013.01); *G01N 2021/8917* (2013.01); *G01N 2201/0626* (2013.01); *G01N 2201/0634* (2013.01); *G01N 2201/0636* (2013.01); *G01N 2201/0637* (2013.01)

(58) Field of Classification Search
USPC .............. 356/238.1, 238.2, 239.1, 429–431; 250/548, 559.01, 559.05, 559.07, 559.08; 348/132; 362/551, 555
See application file for complete search history.

(56) References Cited

U.S. PATENT DOCUMENTS

| | | | | |
|---|---|---|---|---|
| 2003/0132402 | A1* | 7/2003 | Holl | G06K 9/2036 250/556 |
| 2006/0092276 | A1* | 5/2006 | Ariglio | G01N 21/896 348/132 |
| 2007/0279911 | A1* | 12/2007 | Kittelmann | F21L 4/005 362/328 |
| 2012/0218611 | A1 | 8/2012 | Ikari et al. | 358/474 |

OTHER PUBLICATIONS

Written Opinion dated Jul. 11, 2017 in corresponding PCT International Application No. PCT/EP2017/025132.

* cited by examiner

QUALITY CONTROL STATION FOR A SHEET ELEMENT PROCESSING MACHINE AND ILLUMINATION UNIT FOR THE QUALITY CONTROL STATION

CROSS-REFERENCE TO RELATED APPLICATIONS

The present application is a 35 U.S.C. §§ 371 national phase conversion of PCT/EP2017/025132, filed May 17, 2017, which claims priority of European Patent Application No. 16172030.5, filed May 30, 2016, the contents of which are incorporated by reference herein. The PCT International Application was published in the English language.

TECHNICAL FIELD

The invention relates to a quality control station for a sheet element processing machine and to an illumination unit for such quality control station.

TECHNICAL BACKGROUND

The term "sheet element processing machine" is here intended to comprise any machine which is being used for processing sheet elements such as paper, cardboard or similar materials, in particular printing machines, coating machines, laminating machines and converting machines (for example cutting, stamping, folding and/or gluing machines).

It is generally known to control the quality of sheet elements by means of a camera. Generally, the camera captures images of the sheet elements being transported through the quality control station. The captured images are analyzed with respect to many different parameters so as to obtain information whether or not the sheet elements fulfill certain criteria.

In order to allow the camera to capture the desired images, it is necessary to illuminate a viewing area of the camera which is the portion of the sheet element of which an image is being captured. It is important that the illumination unit provides light with an intensity which is as constant as possible.

While it is not too difficult to ensure that a certain, known viewing area is illuminated with a constant intensity, problems automatically arise if the quality control station is intended to receive sheet elements of different height e.g. thin paper and thick cardboard as this automatically result in a change of the "height" of the viewing area, the distance of the upper surface of the sheet element from a surface on which the sheet elements are being supported In a simple example, or assuming that cardboard with a thickness of 12 mm is being inspected, the viewing area is located 11.5 mm higher as compared to a situation where paper with a thickness of 0.5 mm is being inspected.

SUMMARY OF THE INVENTION

The object of the invention is to provide a quality control station which can accommodate different media with different thicknesses without involving too much adaptation.

In order to achieve this object, the invention provides a quality control station for a sheet element processing machine, having at least one camera arranged for capturing images of sheet elements transported through the quality control station, and an illumination unit with at least one light emitter and two reflectors. The illumination unit is configured for directing light onto a viewing area of the camera such that the illumination intensity is constant despite changing media thickness. The invention is based on the idea of illuminating the viewing area of the camera with an intensity which is constant over a comparatively wide zone both vertically and along the direction in which the sheet elements are being advanced. Thus, the illumination intensity is constant irrespective of the viewing area being close to the surface on which the sheet elements are being transported, which is the case with a thin sheet element or being at a certain level above this surface as this is the case with a thick sheet element. Furthermore, the illumination intensity is homogeneous along the transverse direction. Therefore, the quality control station does not have to be adjusted or tuned depending on the thickness of the particular media which is being advanced through the sheet element processing machine.

The illumination unit used in the quality control station can comprise a base carrying the light emitter which extends along a length of the illumination unit, and two reflectors extending along the light emitter and arranged so as to face each other. Each reflector has a parabolic or aspherical contour when viewed in a cross section, in particular a conical contour.

The illumination intensity which is constant over a certain zone is achieved by appropriately superimposing three different portions of the light coming from the light emitter: A first portion of the light is emitted by the light emitter towards the first reflector and is reflected towards the viewing area. A second portion of the light is emitted by the light emitter towards the second reflector and is reflected towards the viewing area. A third portion of the light is emitted by the light emitter directly towards the viewing area. By using the two distinct reflectors, the light reflected with the first and second reflectors onto the viewing area can be adjusted individually so as to finally achieve a constant illumination intensity when the reflected light is superimposed with the light falling directly onto the viewing area, a constant illumination intensity.

The light emitter can be implemented in any form which allows generating light with the desired intensity and wavelength. Preferably, the light emitter is formed from a plurality of LEDs arranged adjacent each other. LEDs are compact and generate very little lost heat which allows incorporating them into a compact illumination unit.

According to a preferred embodiment, the light emitter is arranged immediately adjacent the base. This adds to the compact configuration of the illumination unit and is possible as no reflector is arranged "behind" the light emitter when looking from the viewing area into the illumination unit. This arrangement is also good for thermal power dissipation. The thermal path between the LED (back surface) and the support is very short. Further, a duct for water or air cooling can be integrated into the base.

In view of typical light intensity profiles of LEDs, an opening angle in the order of 10° to 20° is present between an optical plane of the illumination unit and the reflectors. Thus, the light emitted with high intensity along an optical plane of the LED can directly fall onto the viewing area while the light emitted more laterally is redirected by the reflector towards the viewing area.

In order to achieve a uniform illumination of the viewing area over a zone which is approx. 12 mm wide (in the direction in which the sheet elements are being advanced) and/or high, the energy of the light emitter reflected by each of the two reflectors is distributed at a distance in the order of 6 to 10 mm from the optical plane of the illumination unit.

A diffuser can be associated with the illumination unit. This allows achieving a more homogeneous radiance. The diffuser can be for example a holographic diffuser in one direction, perpendicular to the sheet moving direction.

It is possible to use two reflectors which have an identical contour. Depending on the particular requirements, it is also possible to implement small variations of the contour of one reflector as compared to the contour of the other reflector, with these variations however usually being minimal.

The illumination unit preferably extends with a certain length in a direction transverse to the direction in which the sheet elements are being advanced through the quality inspection station. The length of the illumination unit is preferably more than 200 mm so that a wide portion of the viewing area is being illuminated.

If desired, two or more illumination units can be arranged adjacent each other. It is also possible to use more than one camera. In particular, two or more cameras can be used adjacent each other, with each camera capturing images of a portion of the narrow viewing area extending over the entire width of the transfer passage for the sheet elements in the quality inspection station.

According to a preferred embodiment, an optical plane of the reflector is arranged at an angle of approx. 45° with respect to a plane which is perpendicular to the plane in which the viewing area is arranged. This orientation of the optical plane of the reflector results in the zone with the constant illumination intensity having a height which corresponds to its width. As an example, if the zone with the constant illumination intensity has a height of 12 mm (resulting in the surface of thin paper being illuminated with the same intensity as the surface of cardboard as thick as 12 mm), this zone extends, viewed along the direction in which the sheet elements are being transported through the viewing area of the camera) over 12 mm as well. The result of this is that possible tolerances regarding the position of the camera and of the illumination unit in the sheet travel direction do not have much impact on the illumination intensity at a particular point on the surface of the respective sheet element in the viewing area.

Preferably, an optical plane of the camera is arranged at an angle of approx. 20° with respect to a plane which is perpendicular to the plane in which the viewing area is arranged. This has proven advantageous both regarding the image capturing capabilities of the system and regarding the compactness of the assembly comprising the camera and the illumination unit.

For typical inspection conditions in sheet element processing machines, the light emitter can be arranged at a distance of 60 to 120 mm from the viewing area, in particular at a distance in the order of 90 mm.

The above mentioned object is also achieved with an illumination unit adapted for being used in a quality control station, comprising a base carrying at least one light emitter extending along a length of the illumination unit, and two reflectors extending along the light emitter and being arranged so as to face each other. Each of the reflectors has a conic contour when viewed in a cross section. The illumination unit provides an essentially uniform distribution of the irradiance on a rectangular area corresponding to the illuminated field. The illuminated field extends in a media feed direction by a certain distance and the uniform distribution of the irradiance is present at different levels above the illuminated field up to a level which is above the illuminated field by the certain distance.

The invention will now be described with reference to a preferred embodiment which is shown in the enclosed drawings. In the drawings,

DESCRIPTION OF AN EMBODIMENT

Figure 1:
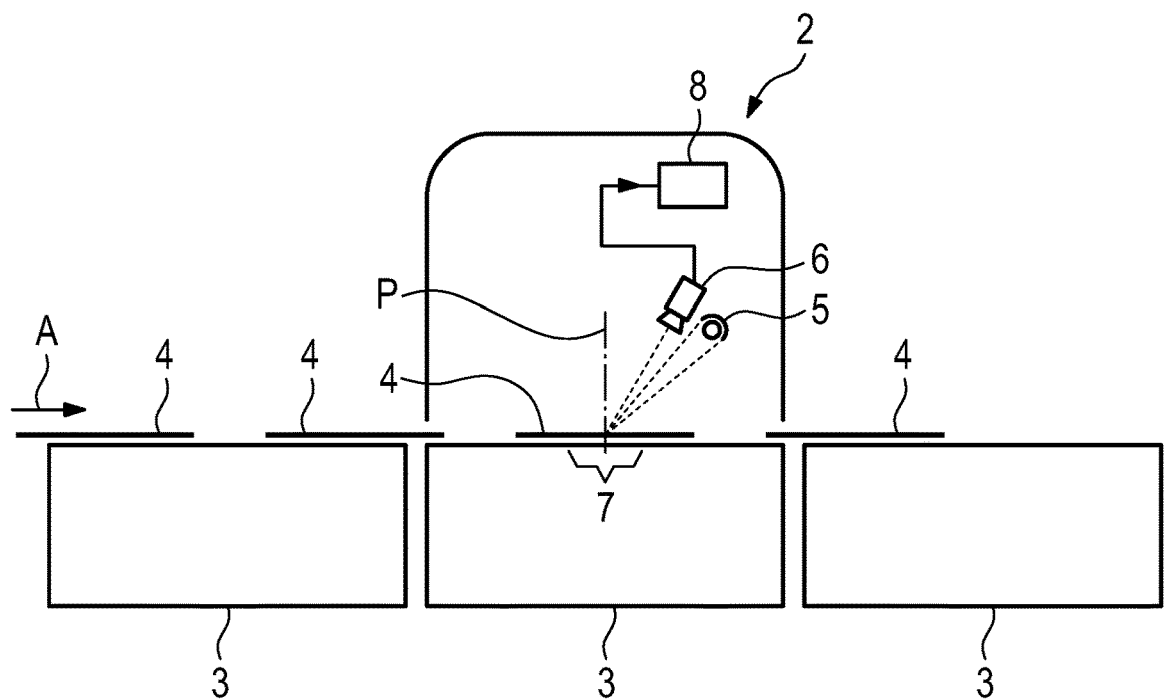
FIG. 1 schematically shows in a side view a quality control station according to an embodiment of the invention employed in a sheet element processing machine.

In FIG. 1, a quality control station 2 is schematically shown, which is employed in a sheet element processing machine of which conveyor tables 3 are shown. The sheet element processing machine can process sheet elements 4 which are being transported in the direction of arrow A. The sheet elements 4 can be sheets of paper, cardboard, a plastic film or a similar material, or they can be in the form of a longer web. The sheet element processing machine can be a printing machine, a stamping machine, a laminating machine, a folding machine, a gluing machine, etc.

The quality control station 2 is used for controlling the quality of the sheet elements 4. Generally stated, an illumination unit 5 is used which directs light onto a surface of a sheet element which is currently being inspected, and a camera 6 is used for capturing an image of the sheet element 4 currently being advanced through the quality control station.

Figure 2:
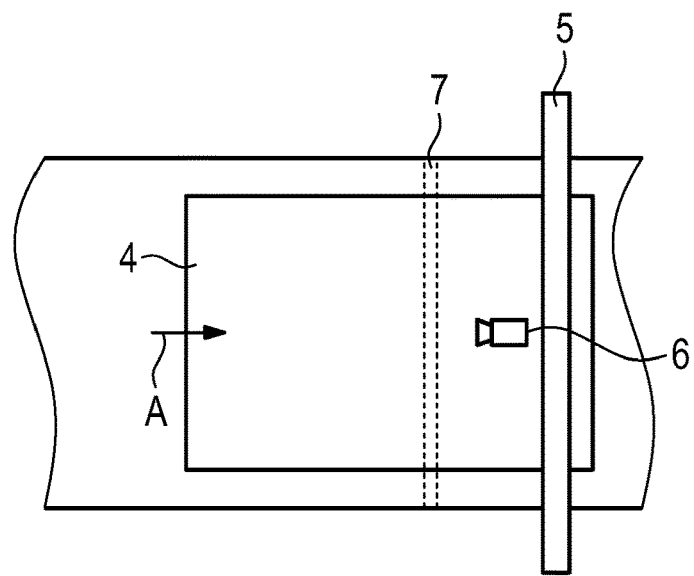
FIG. 2 schematically shows the quality control station of FIG. 1 in a top view.

More precisely, in FIG. 2, camera 6 captures an image in a viewing area 7 which is a very narrow area extending over the entire width of the sheet elements in a direction perpendicular to the direction A along which the sheet elements are being advanced through the quality control station 2.

It is also possible to use more than one illumination unit 5, and it is also possible to use more than one camera 6 in the quality control station 2. In particular, it is possible to use two cameras which are arranged adjacent each other, with a first camera capturing an image of the left half of the sheet within viewing area 7 and the second camera capturing an image of the right half of the sheet within viewing area 7.

The image captured by camera 6 is supplied to a control 8 where it is compared with stored reference images and/or analyzed in various respects. Control 8 then makes a determination whether or not the quality of the respective sheet element 4 satisfies predetermined criteria.

Figure 3:
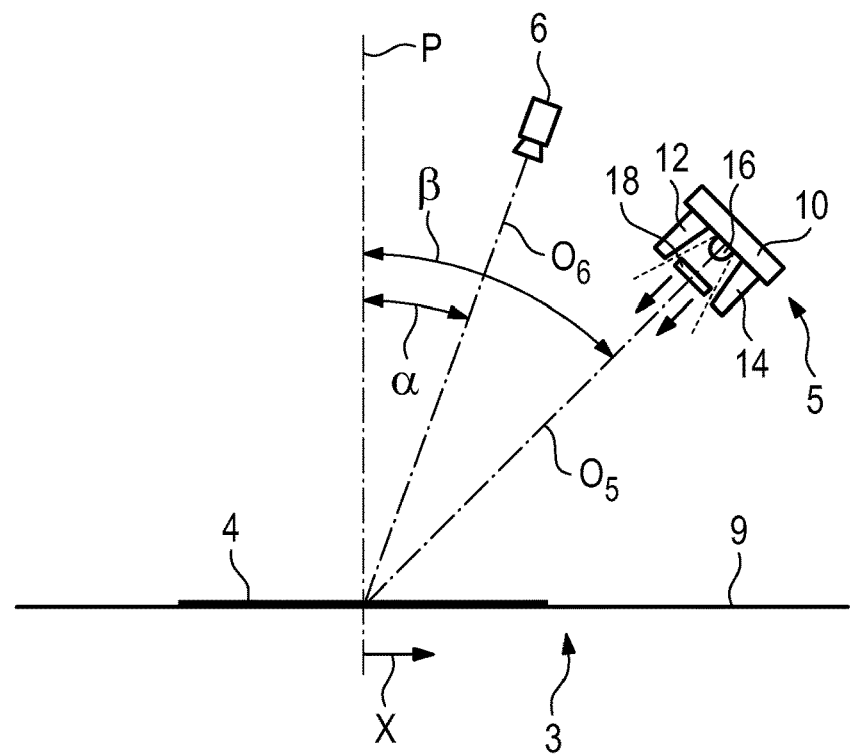
FIG. 3 schematically shows the camera and the illumination unit according to an embodiment of the invention at an enlarged scale.

The orientations of the illumination unit 5 and the camera 6 are shown in more detail in FIGS. 2 and 3.

There is an upper surface 9 of the conveyor table 3. This surface can be considered as being even or flat (at least in the viewing area 7). Accordingly, the upper surface of a sheet element 4 inspected within the viewing area 7 is also considered to be even or flat. A plane extending perpendicularly with respect to surface 9 (and accordingly also perpendicularly with respect to the upper surface of the sheet element 4 within viewing area 7) and also perpendicular to direction A is designated with reference numeral P.

Camera 6 is arranged such that its optical plane $O_6$ is inclined with respect to plane P by an angle α. In a preferred embodiment, the angle α is in the order of 20°. Depending from constructional restraints and from the particular nature of the inspection to be carried out, other angles might alternatively be chosen.

Illumination unit 5 is arranged such that its optical plane $O_5$ is inclined with respect to plane P by an angle β. In a preferred embodiment, the angle β is of the order of 45°. Depending on constructional restraints and on the particular nature of the inspection to be carried out, other angles might be chosen.

As can be seen in FIG. 3, illumination unit 5 comprises a base 10, two reflectors 12, 14 and a light emitter 16.

For some applications, a diffuser 18 can be used. An example of a diffuser is a holographic diffuser with a diffusing function only in the direction perpendicular to the sheet movement. Even though a constant radiance is not necessary in the surface of observation, using a diffuser can be an advantage if a constant radiance along the same surface for a metalized substrate is desirable.

Base 10 is a carrier for the elements of the illumination unit and elongated in a direction which is perpendicular to the plane of FIG. 3. Thus, base 10 extends transverse to the direction A in which the sheet elements 4 are being advanced through the quality inspection station.

A typical length of the illumination unit is of the order of 300 to 400 mm.

Light emitter 16 extends along the longitudinal direction of the base and is adapted for emitting light along the length of the illumination unit. It is possible that the light emitter 16 generates light with an intensity which does not vary along the length of the illumination unit. In practice, the light emitter 16 will usually comprise a plurality of discrete LEDs which are arranged in short intervals close to each other. In combination with diffuser 18, the intensity of light emitted will not (or at least not significantly) vary along the length of the illumination unit 5.

The two reflectors 12, 14 are arranged opposite each other so that the light emitter 16 is positioned between the reflectors 12, 14.

Figure 4:
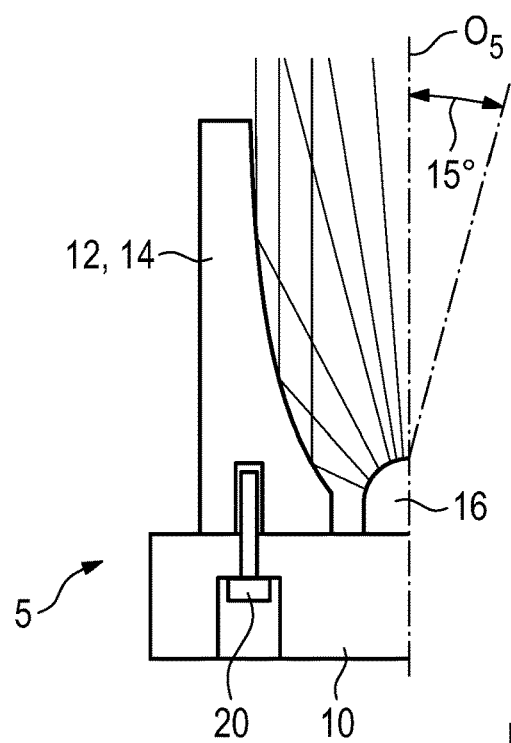
FIG. 4 schematically shows, at an even larger scale, one half of the illumination unit of FIG. 3 at the left side of FIG. 4 and, at the right side, with a typical polar diagram of the light intensity of an LED used as light emitter in the illumination unit.

As can be seen in FIGS. 3 and 4, the contour of each reflector is approximately elliptical or parabolic. The reflectors are arranged generally symmetrically with respect to the optical plane. The surface of each reflector can be described with an equation with is the sum of a conic surface and an aspheric deformation. Both reflectors 12, 14 can be strictly symmetrically identical, or they can be approximately symmetrical with respect to the optical plane, or they can differ slightly in the optical surface form.

The reflectors are separate components manufactured from a suitable material, for example an aluminum alloy or a plastic material, with their reflecting surface being polished or provided with a reflective coating. They can be mounted to base 10 by means of bolts 20.

FIG. 4 shows on the right side, in a polar diagram, the intensity of the light emitted by an LED as is being used in light emitter 16. It can be seen that the intensity of the light is high close to the optical plane $O_5$, in particular in a range between 0° and 15° from the optical plane $O_5$ and that the intensity significantly decreases for larger angles.

On the left side of FIG. 4, the illumination unit 5 can be seen in more detail.

The light emitter 16 is arranged with respect to the reflectors 12, 14 such that a portion of the light generated by the light emitter 16 directly falls onto the sheet element 4 to be inspected and illuminates the viewing area 7. Depending on the geometry of the reflectors 12, 14, this portion corresponds to the light leaving the light emitter 16 at an angle which is between 0° and approx. 18° from the optical plane $O_5$. This portion of the light is shown in FIG. 4 with rays extending obliquely outside the illumination unit 5. The contribution of this light on the viewing area 7 (FIG. 2) is around 25% of the total illumination.

A second and a third portion of the light generated by the light emitter 16, namely the portion leaving the light emitter 16 at an angle above approx. 18° from the optical plane $O_5$, is directed towards the viewing area 7 by the reflectors 12, 14. One of these portions of the light is shown in FIG. 4 with the rays extending parallel to the optical plane $O_5$.

The three portion of the lights, namely the first portion of light originating directly from the light emitter 16, the second portion reflected by reflector 12 and the third portion reflected by reflector 14 are superimposed at the viewing area 7 such that the intensity of the total light is constant over a zone which is several millimeters wide and also several millimeters high.

Figure 5:
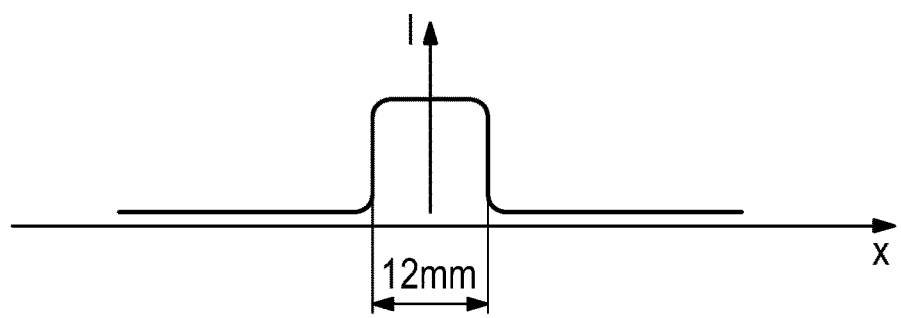
FIG. 5 schematically shows the light intensity in a viewing area receiving light from the illumination unit according to an embodiment of the invention.

FIG. 5 shows the total intensity $I_t$ of the light in the viewing area. It can be seen that the intensity is constant over a zone of 12 mm wide in the x direction, which corresponds to the direction A of travel of the sheet elements 4.

As a result of the orientation of the optical plane $O_5$, the intensity is constant not only in the horizontal direction but also in the vertical direction. The height of the zone in which the intensity is constant is also 12 mm. If the optical plane $O_5$ were arranged at an angle β different from 45°, the width of the zone of constant intensity would be different from its height.

The term "constant intensity" does not require the intensity to be perfectly constant. Rather, the term encompasses small variations of the intensity, provided that the variations are so small that they do not affect the inspection to be made within the different conditions which can occur e.g. change from thin paper to thick cardboard. In practice, variations of the intensity of 3%/mm and more preferably of 0.5%/mm to 1%/mm deviation, and a total of 2% to 5% over the entire zone with constant intensity from a reference point either in the z direction or in the x direction, are considered as "constant".

Figure 6:
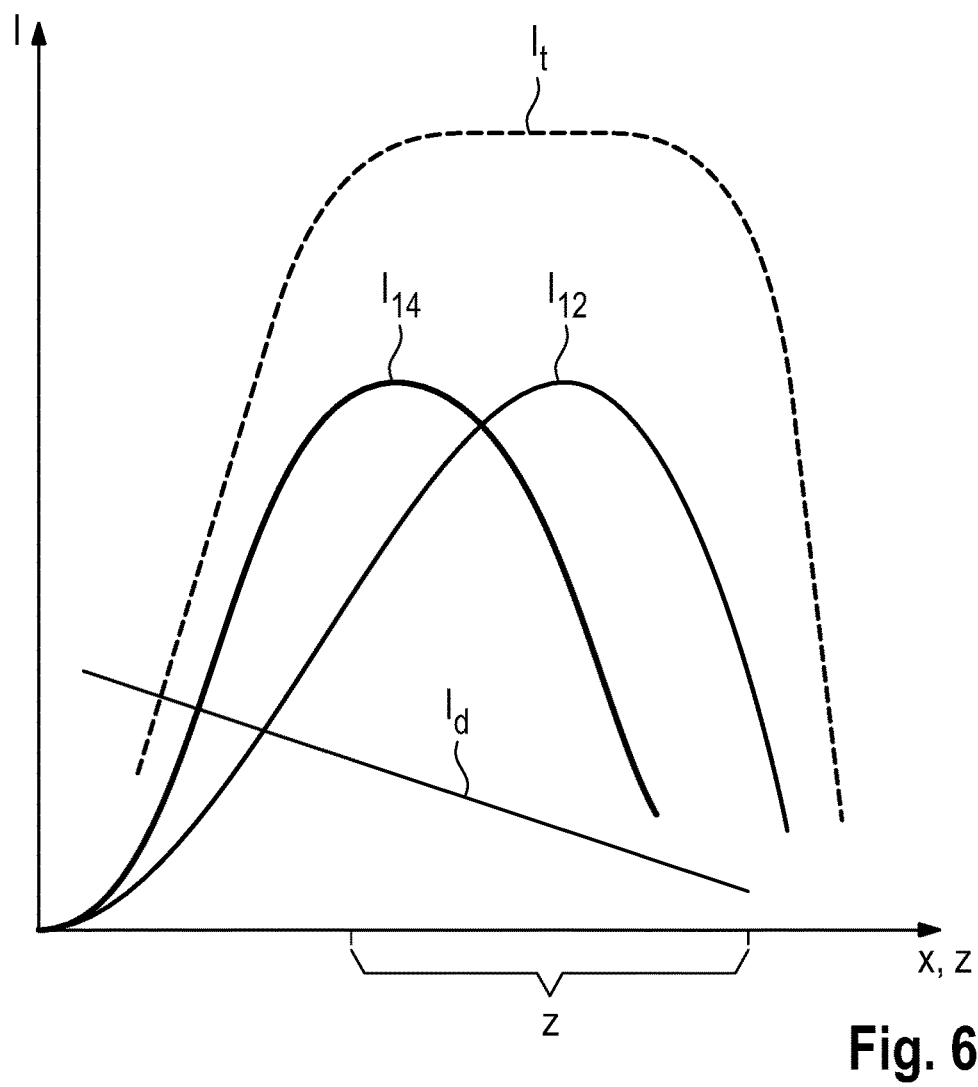
FIG. 6 schematically shows the light intensity in a viewing area received from the individual reflectors and received directly from the light emitter, and the resulting total light intensity.

FIG. 6 shows in more detail how the different portions of the light originating from the light emitter 16 and falling onto the viewing area are superimposed so as to achieve a total intensity $I_t$ which is constant.

Line $I_d$ shows the intensity of the light falling directly from the light emitter 16 onto the top surface of a sheet element 4 in the viewing area.

Line $I_{12}$ shows the intensity of the light being reflected from reflector 12 onto the top surface of a sheet element 4 in the viewing area.

Line $I_{14}$ shows the intensity of the light being reflected from reflector 14 onto the top surface of a sheet element 4 in the viewing area.

It can be seen that the different portions of the light result in a total intensity $I_t$ which is constant over a zone z, which here is 12 mm wide, and can extend at different heights between 0 mm and 12 mm.

The invention claimed is:

1. A quality control station for a sheet element processing machine, the station comprising:
   at least one camera arranged for capturing images of sheet elements transported through the quality control station and;
   an illumination unit comprising at least one light emitter, a first reflector and a second reflector, the illumination unit is configured for directing light onto a viewing area of the camera so that a first portion of the light is emitted by the light emitter towards the first reflector and is reflected towards the viewing area, a second portion of the light is emitted by the light emitter towards the second reflector and is reflected towards the viewing area, and a third portion of the light is emitted by the light emitter directly towards the viewing area such that the illumination intensity of the viewing area is constant despite changing media thickness.

2. The quality control station of claim 1, wherein the illumination unit comprises a base carrying the light emitter, the base extends along a length of the illumination unit; and
   the two reflectors extending along the light emitter and being arranged to face each other, each of the reflectors having a parabolic or aspherical contour when viewed in a cross section.

3. The quality control station of claim 2, wherein the light emitter is arranged immediately adjacent the base.

4. The quality control station of claim 2, wherein the two reflectors have an identical contour.

5. The quality control station of claim 2, wherein the illumination unit has a length of more than 200 mm.

6. The quality control station of claim 2, wherein each of the reflectors has a conical controller.

7. The quality control station of claim 1, wherein the light emitter is comprised of a plurality of LEDs arranged adjacent each other.

8. The quality control station of claim 2, wherein an opening angle on the order of 20° is present between an optical plane ($O_5$) of the illumination unit and the reflectors.

9. The quality control station of claim 1, wherein the illumination unit further comprises a diffuser.

10. The quality control station of claim 1, wherein the reflectors are positioned to have
    an optical plane at an angle of approx. 45° with respect to a plane perpendicular to a plane in which the viewing area is arranged.

11. The quality control station of claim 1, wherein the camera is positioned to have an optical plane at an angle of approx. 20° with respect to a plane perpendicular to a plane in which the viewing area is arranged.

12. The quality control station of claim 1, wherein the light emitter is arranged at a distance of 60 to 120 mm from the viewing area.

13. The illumination unit configured for being used in a quality control system of claim 1.

14. An illumination unit configured for use in a quality control station, the illumination unit comprising:
    a base carrying at least one light emitter extending along a length of the illumination unit, and two reflectors extending along the light emitter so as to be illuminated by the light emitter and to reflect light therefrom, the two reflectors being arranged to face each other;
    each reflector has a conic contour when viewed in a cross section;
    the illumination unit being configured for providing an essentially uniform distribution of the irradiance on a rectangular area corresponding to an illuminated field, the illuminated field extending in a media feed direction a selected distance,
    wherein the illumination unit is positioned and configured to provide the essentially uniform distribution of the irradiance at different levels above the illuminated field up to a level which is above the illuminated field by the selected distance.

* * * * *